(12) United States Patent  
Vess

(10) Patent No.: US 7,825,289 B2
(45) Date of Patent: Nov. 2, 2010

(54) WOUND DRESSING ADHESIVE COMPRESSION DEVICE

(75) Inventor: Mark A. Vess, Hanson, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 100 days.

(21) Appl. No.: 12/122,261

(22) Filed: May 16, 2008

(65) Prior Publication Data

US 2009/0287132 A1    Nov. 19, 2009

(51) Int. Cl.
- A61F 13/00    (2006.01)
- A61F 13/02    (2006.01)
- A61L 15/00    (2006.01)
- A61L 15/16    (2006.01)

(52) U.S. Cl. .......................... 602/53; 602/48; 424/445; 424/448; 604/304; 604/307

(58) Field of Classification Search .................. 602/53, 602/48, 46; 424/443–449, 78.05, 78.06, 424/78.07; 604/304, 307, 289, 313
See application file for complete search history.

(56) References Cited

U.S. PATENT DOCUMENTS

| | | | |
|---|---|---|---|
| 4,717,382 A | 1/1988 | Clemens et al. | |
| 4,773,408 A | 9/1988 | Cilento et al. | |
| 4,997,438 A | 3/1991 | Nipper | |
| 5,264,218 A | 11/1993 | Rogozinski | |
| 5,817,145 A | 10/1998 | Augustine et al. | |
| 5,986,163 A | 11/1999 | Augustine | |
| 6,106,507 A | 8/2000 | Botten et al. | |
| 7,103,921 B1 | 9/2006 | Shoemaker | |
| 7,214,202 B1 | 5/2007 | Vogel et al. | |
| 7,329,792 B2 | 2/2008 | Buckman et al. | |
| 7,534,927 B2 * | 5/2009 | Lockwood et al. | ............ 602/46 |

| | | | |
|---|---|---|---|
| 2001/0043943 A1 | 11/2001 | Coffey et al. | |
| 2003/0023286 A1 | 1/2003 | Augustine et al. | |
| 2003/0208149 A1 | 11/2003 | Coffey et al. | |

(Continued)

FOREIGN PATENT DOCUMENTS

WO    94/20041    9/1994

(Continued)

OTHER PUBLICATIONS

European Search Report, Application No. EP 09 16 0474 dated Apr. 26, 2010.

Primary Examiner—Patricia M Bianco
Assistant Examiner—Ophelia Hawthorne
(74) Attorney, Agent, or Firm—Elizabeth A. O'Brien, Esq

(57) ABSTRACT

An apparatus for promoting the healing of a wound includes a pressure-sensitive adhesive disposed around a periphery of the wound, and a membrane layer in positioned over the wound with a lower surface in contact with the pressure-sensitive adhesive to form a substantially fluid-tight seal to define reservoir over the wound in which a negative pressure may be maintained. In fluid communication with the reservoir is a vacuum source suitable for providing an appropriate negative pressure to the reservoir to stimulate healing of the wound. A resilient member is placed over an upper surface of the membrane layer, and a compression member is configured to apply a compressive force to the resilient member. The resilient member distributes the compressive force to the membrane layer to reinforce the fluid tight-seal.

12 Claims, 2 Drawing Sheets

U.S. PATENT DOCUMENTS

| | | |
|---|---|---|
| 2004/0097860 A1* | 5/2004 | Tauber ................. 602/75 |
| 2005/0148913 A1 | 7/2005 | Weston |
| 2005/0165445 A1 | 7/2005 | Buckman et al. |
| 2006/0029650 A1 | 2/2006 | Coffey |
| 2006/0079852 A1 | 4/2006 | Bubb et al. |
| 2006/0253089 A1 | 11/2006 | Lin |
| 2007/0027414 A1 | 2/2007 | Hoffmann et al. |
| 2007/0161937 A1 | 7/2007 | Aali |
| 2007/0161938 A1 | 7/2007 | Aali |
| 2007/0275077 A1 | 11/2007 | Arias |
| 2008/0003274 A1 | 1/2008 | Kaiser |

FOREIGN PATENT DOCUMENTS

| | | |
|---|---|---|
| WO | 2006114637 | 11/2006 |

* cited by examiner

WOUND DRESSING ADHESIVE COMPRESSION DEVICE

BACKGROUND

1. Technical Field

The present disclosure relates generally to the treatment of wounds, and in particular to an apparatus for applying compression to a wound dressing to maintain contact between the dressing and a patient's skin for a treatment such as negative wound pressure therapy.

2. Background of Related Art

Wound dressings are generally placed over a wound to protect and promote healing of the wound. One type of wound dressing consists essentially of a thin membrane or cover layer formed of a polymer or similar material. An underside of the membrane may be coated with a pressure-sensitive adhesive to adhere the dressing to healthy skin surrounding the wound. The dressing may thus provide an effective bacterial barrier to protect the wound from contamination. Because of their extremely elastic nature, thin polymeric film dressings may readily conform to irregular contours of a patient's skin while promoting patient movement and comfort. This type of dressing may also be sufficiently transparent to permit visual inspection of the wound without the need for removing the dressing and exposing the wound to contaminants in the environment.

One technique to use a membrane cover layer may be described as negative wound pressure therapy (NWPT). The membrane layer may be positioned to form a substantially fluid-tight seal with the skin surrounding the wound to define a reservoir over the wound where a negative pressure may be maintained. The reservoir subjects the wound to a sub-atmospheric pressure to effectively draw wound fluid, including liquid exudates, from the wound without the continuous use of a vacuum pump. Hence, vacuum pressure may be applied once, or in varying intervals depending on the nature and severity of the wound. This technique has been found to promote blood flow to the wound area, stimulate the formation of granulation tissue and encourage the migration of healthy tissue over the wound.

The evacuation cycles of an NWPT treatment may subject the dressing to repeated changes of size and shape, tending to cause the dressing to become detached from the skin. Leaks may also form between the skin and dressing due to extraordinary patient movement, or when the wound is located on a part of the body where adhesives do not work well. For example, a body portion populated with dense body hair, wrinkled, oily or contaminated skin may prove to be a challenging location to maintain a fluid tight seal with an adhesively coated membrane layer. Any unintended leaks can frustrate the effectiveness of an NWPT treatment. Accordingly, an apparatus to supplement the adhesion of a dressing would be beneficial.

SUMMARY

An apparatus for promoting the healing of a wound includes a pressure-sensitive adhesive disposed around a periphery of the wound, and a membrane layer in positioned over the wound with a lower surface thereof in contact with the pressure-sensitive adhesive such that a substantially fluid-tight seal is formed to define reservoir over the wound in which a negative pressure may be maintained. In fluid communication with the reservoir is a vacuum source suitable for providing an appropriate negative pressure to the reservoir to stimulate healing of the wound. A resilient member is placed over an upper surface of the membrane layer, and a compression member is configured to apply a compressive force to the resilient member such that the resilient member distributes the compressive force to the membrane layer to reinforce the fluid tight-seal.

The resilient member may be formed from an open cell foam material generally in the shape of an annular ring. The resilient member may also include an adhesive coating on an undersurface thereof such that the resilient member may be affixed to the membrane layer in the absence of the compression member. An access passage formed through a lateral side of the resilient member may to facilitate passage of a fluid conduit.

The compression member may comprise a stretchable fabric bandage applied over the resilient member and wrapped around a body portion to provide the compressive force to the resilient member. Alternatively, the compression member may comprise a surgical tape.

The membrane layer may be substantially transparent such that a visual assessment of wound conditions may be made with the resilient member in place.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION

Figure 1:
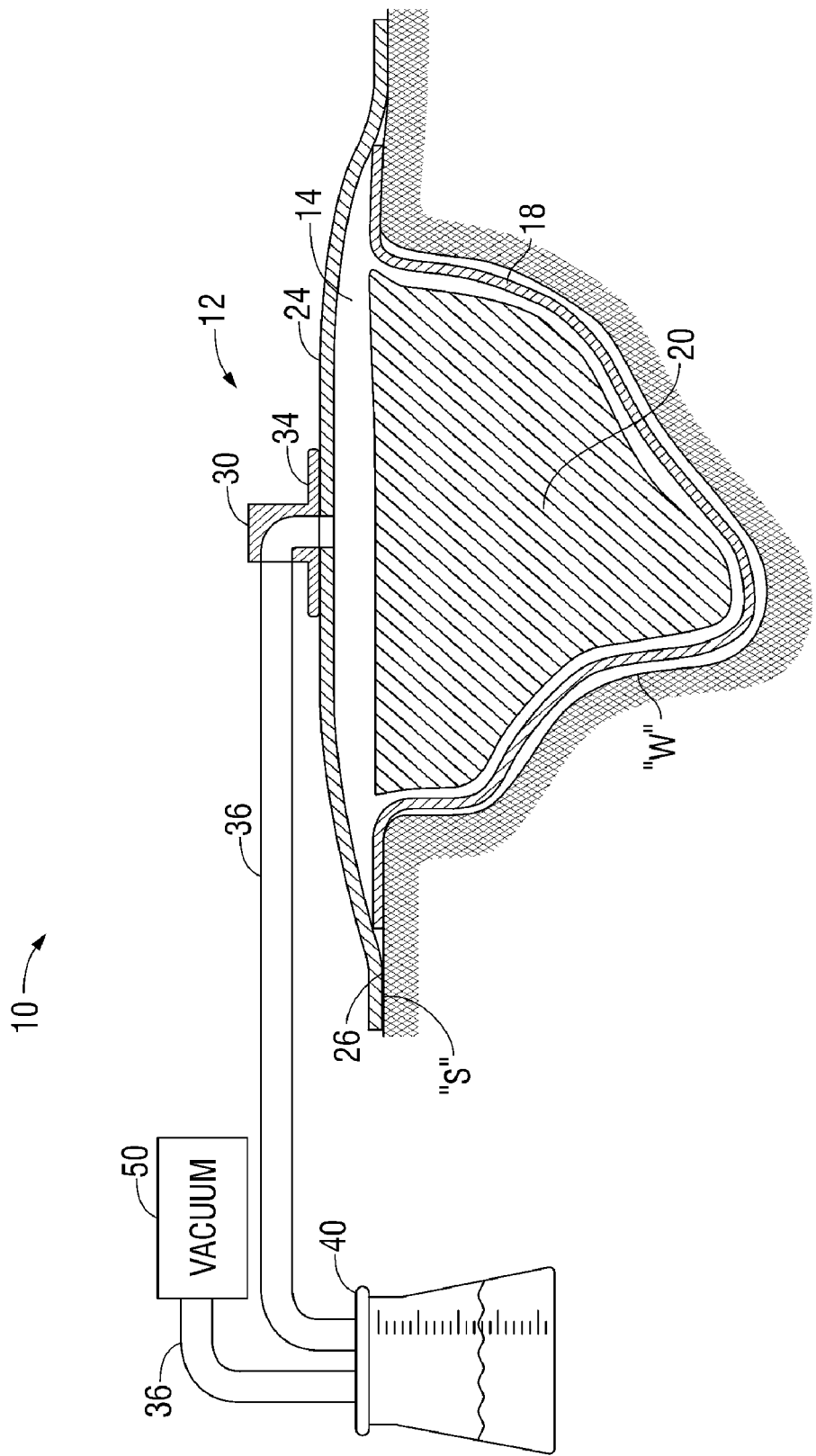
FIG. 1 is a cross sectional view of a NWPT apparatus for use on a wound "w" surrounded by healthy skin "s"

Referring initially to FIG. 1, an NWPT apparatus is depicted generally as 10 for use on a wound "w" surrounded by healthy skin "s." The NWPT apparatus 10 includes a wound dressing 12 positioned relative to the wound "w" to define a reservoir 14 in which a negative pressure appropriate to stimulate healing may be maintained.

Wound dressing 12 includes a contact layer 18 positioned in direct contact with the bed of wound "w" and may be formed from perforated film material. An appropriate perforated material permits the negative pressure applied to the reservoir to penetrate into the wound "w," and also permits exudates to be drawn through the contact layer 18. Passage of wound fluid through the contact layer 18 is preferably unidirectional such that exudates do not flow back into the wound bed. Unidirectional flow may be encouraged by conical or directional apertures formed in the contact layer 18, or a lamination of materials having absorption properties differing from those of contact layer 18. A non-adherent material may be selected such that contact layer 18 does not tend to cling to the wound "w" or surrounding tissue when it is removed. One exemplary material that may be used as a contact layer 18 is sold under the trademark VENTEX® by Kendall Corp., a division of Covidien.

Additionally, agents such as hydrogels and medicaments may be bonded or coated to the contact layer 18 to reduce bioburden in the wound, promote healing and reduce pain associated with changes or removal of the dressing 12. Medicaments include, for example, antimicrobial agents, growth factors, antibiotics, analgesics, and the like. Furthermore, when an analgesic is used, the analgesic could include a mechanism that would allow the release of that agent prior to dressing removal or change.

Wound filler 20 is positioned in the wound "w" over the contact layer 18 and is intended to wick wound fluids and exudates away from the wound "w." Wound filler 20 is cut to a shape that is conformable to the shape of wound "w," and may be packed up to the level of healthy skin "s," or alternatively, wound filler 20 may overfill the wound "w." An absorbent material such as non-woven gauze, reticulated foam, or alginate fibers may be used for filler 20 to draw away any exudates that migrate through contact layer 18. An antimicrobial dressing sold under the trademark KERLIX® by Kendall Corp., a division of Covidien, may be suitable for use as filler 20. To prevent adhesion to the wound "w," the filler 20 may also comprise a material configured such that any stray fibers do not tend to protrude through pores formed in contact layer 18 where they may become engulfed by newly forming granulation tissue. One particular type of material exhibiting this characteristic is formed of continuous filaments comprising either natural or man-made fibers. Continuous filaments include those relatively long strands of a synthetic material such as nylon, rayon, etc., which may offer a smooth continuous outer surface substantially free of the protruding fibrils commonly associated with natural materials such as cotton. The use of continuous filaments of a hydrophobic material such as polyolefin may permit a complete removal of filler 20 when the dressing 12 is changed without re-injuring the wound "w."

Wound dressing 12 also includes a membrane layer 24. Membrane layer 24 may be positioned over the wound "w" to form a substantially fluid-tight seal with the surrounding skin "s" at the periphery 26 of the wound "w." Thus, membrane layer 24 may act as both a microbial barrier to prevent contaminants from entering the wound "w," and also a fluid barrier maintaining the integrity of vacuum reservoir 14. Membrane layer 24 is preferably formed from a moisture vapor permeable membrane to promote the exchange of oxygen and moisture between the wound "w" and the atmosphere, and is preferably transparent to permit a visual assessment of wound conditions without requiring removal of the membrane layer 24. Membrane layer 24 may have an adhesive on its underside to facilitate securement to the skin about the wound "w". An exemplary non-porous, flexible material includes the transparent dressing manufactured under the trademark Polyskin II by Tyco Healthcare Group LP (d/b/a Covidien). The top layer 110 may be a transparent, non-porous material and provides a barrier to microbes and fluid containment.

A vacuum port 30 having a flange 34 may also be included in wound dressing 12 to facilitate connection of the wound dressing 12 to fluid conduit 36. Fluid conduit 36 defines a fluid flow path leading through the apparatus 10. The vacuum port 30 may be configured as a rigid or flexible, low-profile component, and may be adapted to receive a fluid conduit 36 in a releasable and fluid-tight manner. An adhesive on the underside of flange 34 may provide a mechanism for affixing the vacuum port 30 to the dressing 12, or alternatively flange 34 may be positioned within reservoir 14 (not shown) such that an adhesive on an upper side of the flange 34 affixes the vacuum port 30. However it is affixed to the dressing, a hollow interior of the vacuum port 30 provides fluid communication between the fluid conduit 36 and the reservoir 14. Vacuum port 30 may be provided as a pre-affixed component of dressing 12, as a component of fluid conduit 36 or entirely independently. Alternatively, vacuum port 30 may be eliminated from dressing 12 if other provisions are made for providing fluid communication with the fluid conduit 36.

Fluid conduit 36 extends from the vacuum port 30 to provide fluid communication between the reservoir 14 and collection canister 40. Any suitable conduit may be used for fluid conduit 36 including those fabricated from flexible elastomeric or polymeric materials. Fluid conduit 36 may connect to the vacuum port 30, the canister 40, or other apparatus components by conventional air tight means such as friction fit, bayonet coupling, or barbed connectors. The conduit connections may be made permanent, or alternatively a quick-disconnect or other releasable means may be used to provide some adjustment flexibility to the apparatus 10.

Collection canister 40 may comprise any container suitable for containing wound fluids. For example, a rigid bottle may be used as shown or alternatively a flexible polymeric pouch may be appropriate. Collection canister 40 may contain an absorbent material to consolidate or contain the wound drainage or debris. For example, super absorbent polymers (SAP), silica gel, sodium polyacrylate, potassium polyacrylamide or related compounds may be provided within canister 40. At least a portion of canister 40 may be transparent to assist in evaluating the color, quality or quantity of wound exudates. A transparent canister may thus assist in determining the remaining capacity of the canister or when the canister should be replaced.

Leading from collection canister 40 is another section of fluid conduit 36 providing fluid communication with vacuum source 50. Vacuum source 50 generates or otherwise provides a negative pressure to the NWPT apparatus 10. Vacuum source 50 may comprise a peristaltic pump, a diaphragmatic pump or other mechanism that is biocompatible and draws fluids, e.g. atmospheric gasses and wound exudates, from the reservoir 14 appropriate to stimulate healing of the wound "w." Preferably, the vacuum source 50 is adapted to produce a sub-atmospheric pressure in the reservoir 14 ranging between about 20 mmHg and about 500 mmHg, more preferably, about 75 mmHg to about 125 mmHg. One suitable peristaltic pump is the Kangaroo PET Eternal Feeding Pump manufactured by Kendall Corp., a division of Covidien.

Figure 2:
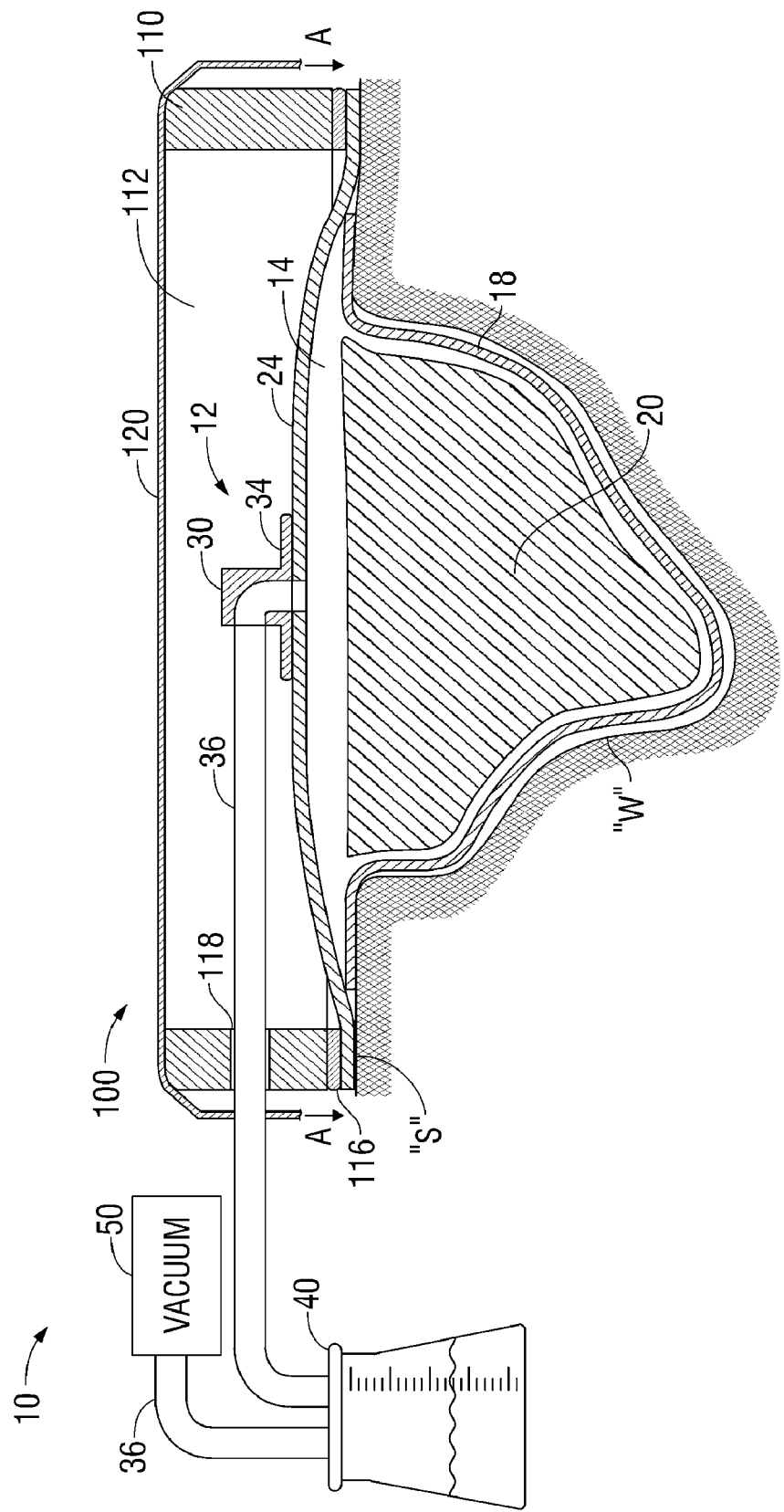
FIG. 2 is a cross sectional view of a membrane adhesive compression device placed over a membrane layer of the NWPT apparatus of FIG. 1.

Referring now to FIG. 2, the adherence of dressing 12 to skin "s" is supplemented by a membrane adhesive compression device 100. Membrane adhesive compression device 100 includes a resilient member 110 formed from a low rigidity material such as an open cell foam, sponge, elastomer or similar material. The resilient member 110 is configured as an annulus approximating the size and shape of the membrane layer 24, thus permitting the resilient member 110 to be positioned over the periphery 26 of the wound "w" where the membrane layer 24 makes contact with the skin "s." A central void 112 in the resilient member 110 accommodates vacuum port 30 and provides a space over the wound "w" in which the membrane layer 24 may rise and fall in response to the evacuation cycles of an NWPT treatment. The central void 112 may extend through the resilient member 110 to an upper surface such that resilient member 110 forms an open ring or annulus. Such an open structure permits a visual assessment of the condition of wound "w" to be made through a transparent membrane layer 24 without the need for removing the resilient member 110.

An adhesive 116 may be provided on a lower surface of the resilient member 110 to maintain the position of the resilient member 110 over the wound dressing 12. A fluid tight seal is not necessarily formed by adhesive 116, and thus a mild or releasable adhesive 116 may be appropriate. In one embodiment, resilient member 110 has an adhesive coating. In the alternative, an adhesive may be applied at the operative site by the clinician. Resilient member 110 may also include an access passage 118 extending through a lateral side thereof. Access passage 118 is positioned to facilitate passage of fluid conduit 36 to canister 40.

Placed over the resilient member 110 is a compression member 120, which is placed in contact with an upper surface of the resilient member 110 to provide a compressive force thereto. Compression member 120 may comprise various structures including, for example, a stretch-fabric bandage. If wound "w" is located on the patient's leg, a stretch-fabric bandage may be wrapped around both the leg and the resilient member 110 such that the resilient member 110 is compressed in the direction of arrows "A." Alternative structures for compression member 120 include surgical tape applied between the upper or lateral surfaces of the compression member and the skin "s" surrounding the wound "w." Compression member 120 may be secured to the skin via adhesives, clamps or the like.

In use, the membrane adhesive compression device 100 may be placed on a patient once the wound dressing 12 is applied. The compressive force supplied by the compression member 120 is transferred through the resilient member 110 to press against the membrane layer 24. This force tends to support and reinforce the air tight seal formed by the pressure sensitive adhesive on the underside of the membrane layer 24. The resiliency of resilient member 110 permits a consistent pressure to be applied to the membrane layer 24 to discourage the separation of the membrane layer 24 from the skin "s" even through extraordinary patient movement. Also the resiliency of resilient member 110 provides a cushion to help to ensure that an excessive force is not experienced by the area surrounding the wound "w."

At such time the wound "w" is inspected, the compression member 120 may be removed to reveal the central void 112. A transparent membrane layer 24 may then permit a visual assessment to be made of wound conditions without the need to remove the either the resilient member 110 or the membrane layer 24. If it is determined that wound conditions are such that a continuation of the NWPT treatment would be beneficial, the compression member 120 may simply be replaced and the NWPT treatment may continue uninterrupted.

Although the foregoing disclosure has been described in some detail by way of illustration and example, for purposes of clarity or understanding, it will be obvious that certain changes and modifications may be practiced within the scope of the appended claims.

What is claimed is:

1. An apparatus to promote healing of a wound comprising:
   a substantially non-porous membrane layer including an adhesive on an underside thereof, the adhesive extending around a periphery of the membrane layer for forming a substantially fluid-tight seal around a periphery of the wound;
   a vacuum source in fluid communication with the wound, the vacuum source suitable for providing an appropriate negative pressure to stimulate healing of the wound;
   a resilient member disposed over an upper surface of the membrane layer and around the periphery of the membrane layer, the resilient member including a central void extending to the periphery of the membrane layer; and
   a compression member configured to apply a compressive force to the resilient member such that the resilient member distributes the compressive force to the membrane layer to reinforce the fluid-tight seal.

2. The apparatus according to claim 1, wherein the vacuum source is in fluid communication with the wound through a vacuum port coupled to the membrane layer, the vacuum port configured to receive a fluid conduit.

3. The apparatus according to claim 2, wherein the vacuum port is disposed within the central void of the resilient member.

4. The apparatus according to claim 1, wherein the central void of the resilient member extends to an upper surface of the resilient member such that the resilient member forms an annulus.

5. An apparatus to promote healing of a wound comprising:
   a substantially non-porous membrane layer including an adhesive on an underside thereof for forming a substantially fluid-tight seal around the wound to define a reservoir in which a negative pressure may be maintained;
   a vacuum source in fluid communication with the reservoir, the vacuum source suitable for providing an appropriate negative pressure to the reservoir to stimulate healing of the wound;
   a resilient member disposed on an exterior of the reservoir and around the periphery of the wound; and
   a compression member configured to apply a compressive force to the resilient member such that the resilient member distributes the compressive force to the membrane layer to reinforce the fluid-tight seal.

6. The apparatus according to claim 5, wherein the resilient member comprises an open cell foam material.

7. The apparatus according to claim 5, wherein the resilient member comprises an annular ring.

8. The apparatus according to claim 5, wherein the resilient member includes an adhesive coating on an undersurface thereof such that the resilient member may remain in place in the absence of the compression member.

9. The apparatus according to claim 5, wherein the resilient member includes an access passage formed in a lateral side thereof for passage of a fluid conduit.

10. The apparatus according to claim 5, wherein the compression member comprises a stretchable fabric bandage applied over the resilient member and wrapped around a body portion to provide the compressive force to the resilient member.

11. The apparatus according to claim 5, wherein the compression member comprises a surgical tape.

12. The apparatus according to claim 5, wherein the membrane layer is substantially transparent such that a visual assessment of wound conditions may be made with the resilient member in place.

\* \* \* \* \*